US010894021B2

(12) United States Patent
Chan et al.

(10) Patent No.: US 10,894,021 B2
(45) Date of Patent: Jan. 19, 2021

(54) COMPOSITIONS OF XANTHORRHIZOL AND TOCOCHROMANOL (TOCOTRIENOL), AND METHODS OF USE

(71) Applicant: American River Nutrition, LLC, Hadley, MA (US)

(72) Inventors: Darren Heiy-Yin Chan, Johns Creek, GA (US); Chappell Rebecca Madhani, Kennesaw, GA (US); Manal Elfakhani, Alpharetta, GA (US); Sophie Thora Yount, Canton, GA (US); Huanbiao Mo, Atlanta, GA (US); Barrie Tan, Hadley, MA (US)

(73) Assignee: AMERICAN RIVER NUTRITION, LLC, Hadley, MA (US)

( * ) Notice: Subject to any disclaimer, the term of this patent is extended or adjusted under 35 U.S.C. 154(b) by 0 days.

(21) Appl. No.: 16/152,417

(22) Filed: Oct. 5, 2018

(65) Prior Publication Data
US 2019/0105284 A1 Apr. 11, 2019

Related U.S. Application Data

(60) Provisional application No. 62/568,323, filed on Oct. 5, 2017.

(51) Int. Cl.
| A61K 31/05 | (2006.01) |
| A61K 9/00 | (2006.01) |
| A61K 31/045 | (2006.01) |
| A61K 31/355 | (2006.01) |
| A61K 31/12 | (2006.01) |
| A61K 36/9066 | (2006.01) |
| A61K 31/353 | (2006.01) |
| A61K 31/015 | (2006.01) |

(52) U.S. Cl.
CPC ............ A61K 31/05 (2013.01); A61K 9/0053 (2013.01); A61K 31/015 (2013.01); A61K 31/045 (2013.01); A61K 31/12 (2013.01); A61K 31/353 (2013.01); A61K 31/355 (2013.01); A61K 36/9066 (2013.01)

(58) Field of Classification Search
CPC .................................................... A61K 31/05
See application file for complete search history.

(56) References Cited

U.S. PATENT DOCUMENTS

| 8,906,960 B2 * | 12/2014 | Nesaretnam | ......... A61K 31/045 514/458 |
| 2012/0329864 A1 | 12/2012 | Nesaretnam et al. | |
| 2013/0274343 A1 | 10/2013 | Desphande et al. | |
| 2016/0089320 A1 | 3/2016 | Tan | |

OTHER PUBLICATIONS

Oon et al., Xanthorrhizol: a review of its pharmacological activities and anticancer properties, Cancer Cell Int (2015) 15:100.*
Du et al., Facile Total Synthesis of Xanthorrhizol, Natural Product Communications vol. 6 (2) 2011, 167-169.*
Cheah, Y. H., H. L. Azimahtol, et al. (2006). "Xanthontizol exhibits antiproliferative activity on MCF-7 breast cancer cells via apoptosis induction." Anticancer Res 26(6B): 4527-4534.
Cheah, Y. H., F. J. Nordin, et al. (2009). "Combined xanthorrhizol-curcumin exhibits synergistic growth inhibitory activity via apoptosis induction in human breast cancer cells MDAAA-MB-231." Cancer Cell Int 9: 1.
Cheah, Y. H., F. J. Nordin, et al. (2008). "Antiproliferative property and apoptotic effect of xanthorrhizol on MDA-MB-231 breast cancer cells." Anticancer Res 28(6A): 3677-3689.
Choi, M. A., S. H. Kim, et al. (2005). "Xanthontizol, a natural sesquiterpenoid from Curcuma xanthorrhiza, has an anti-metastatic potential in experimental mouse lung metastasis model." Biochem Biophys Res Commun 326(1): 210-217.
Fernandes, N. V., H. Yeganehjoo, et al. (2013). "Geranylgeraniol suppresses the viability of human DU145 prostate carcinoma cells and the level of HMG CoA reductase." Exp Biol Med (Maywood) 238(11): 1265-1274.
He, L., H. Mo, et al. ( 1997). "Isoprenoids suppress the growth of murine B 16 melanomas in vitro and in vivo." J Nutr 127(5): 668-674.
HMPC, E. m. a. C. o. H. M. P. E. m. a. (2014). Assessment report on Curcuma xanthorrhiza Roxb. (C. xanthorrhiza D. Dietrich), rhizoma. E m. agency. Jan. 28.
Ismail, N., A.H. Pihie, et al. (2005). "Xanthorrhizol induces apoptosis via the upÂ-regulation of bax and p53 in HeLa cells." Anticancer Res 25(3B): 2221-2227.
Itokawa, H., F Hirayama, et al. (1985). "Studies on the antitumor bisabolane sesquiterpenoids isolated from Curcuma xanthorrhiza." Chem Pharm Bull (Tokyo) 33(8): 3488-3492.
Kang, Y. J., K. K. Park, et al. (2009). "Xanthorrhizol, a natural sesquiterpenoid, induces apoptosis and growth arrest in HCTI 16 human colon cancer cells." J Pharmacol Sci 111(3): 276-284.
Katuru, R., N. V. Fernandes, et al. (2011). "Mevalonate depletion mediates the suppressive impact of geranylgeraniol on murine BI6 melanoma cells." Exp Biol Med (Maywood) 236(5): 604-613.

(Continued)

Primary Examiner — Svetlana M Ivanova
(74) Attorney, Agent, or Firm — Troutman Pepper Hamilton Sanders LLP

(57) ABSTRACT

A dietary supplement composition provided synergistic effects of xanthorrhizol and tocotrienol on malignancies. A blend of xanthorrhizol and delta tocotrienol achieved 69% growth suppression of melanoma, exceeding the sum of individual effects. In prostate cancer, 90% growth suppression was achieved by a blend of xanthorrhizol and delta tocotrienol; however, the same 90% of growth suppression was achieved by 3-fold xanthorrhizol and 1.8-fold delta tocotrienol respectively, which indicated synergistic impact of the two agents. Mechanisms of action for the anticancer property showed synergism of xanthorrhizol and tocotrienol-mediated cancer growth suppression was attributed to cell cycle arrest, at the G1 phase of cell cycle, and apoptosis. This novel dietary supplement combination of xanthorrhizol to tocotrienol (1:1 to 10:1) may provide benefits to individuals consuming it on a regular or periodic basis.

17 Claims, 7 Drawing Sheets

(56) References Cited

OTHER PUBLICATIONS

McAnally, J. A., J. Gupta, et al. (2007). "Tocotrienols potentiate lovastatin-mediated growth suppression in vitro and in vivo." Exp Biol Med (Maywood) 232(4): 523-531.

Mo, H. and C. E. Elson (1999). "Apoptosis and cell-cycle arrest in human and murine tumor cells are initiated by Isoprenoids." J Nutr 129(4): 804-813.

Mo, H. and C. E. Elson (2004). "Studies of the isoprenoid-mediated inhibition of mevalonate synthesis applied to cancer chemotherapy and chemoprevention." Exp Biol Med (Maywood) 229(7): 567-585.

Oon, S. F., M. Nallappan, et al. (2015). "Xanthorrhizol: a review of its pharmacological activities and anticancer properties." Cancer cell international 15(1): 100.

Sever, N., B. L Song, et al. (2003). "Insig-dependent ubiquitination and degradation of mammalian 3-hydroxy-3- methylglutaryl-CoA reductase stimulated by sterols and geranylgeraniol." J Biol Chem 278(52): 52479-52490.

Song, B. L. and R. A. DeBose-Boyd (2006). "Insig-dependent ubiquitination and degradation of 3-hydroxy-3-methylglutaryl coenzyme a reductase stimulated by 8- and yÂ-tocotrienols." J Biol Chem 281(35): 25054-25061.

Tallarida, R. J. (2006). "An overview of drug combination analysis with isobolograms." J Pharmacol Exp Ther 319(1): 1-7.

Yeganehjoo, H., R. DeBose-Boyd, et al. (2017). "Synergistic impact of d-8-tocotrienol and geranylgeraniol on the growth and HMG CoA reductase of human DU145 prostate carcinoma cells." Nutr Cancer 69(4): 682-691.

\* cited by examiner

| Total dose (μmol/L) | d-δ-Tocotrienol (μmol/L) | Xanthorrhizol (μmol/L) | CI Value |
|---|---|---|---|
| 60 | 10 | 50 | 0.94 |
| 120 | 20 | 100 | 0.61 |

Figure 7

COMPOSITIONS OF XANTHORRHIZOL AND TOCOCHROMANOL (TOCOTRIENOL), AND METHODS OF USE

CROSS-REFERENCE TO RELATED APPLICATIONS

This is a Non-Provisional application, which claims priority to U.S. Provisional Application No. 62/568,323, which was filed on Oct. 5, 2017; the contents of which are all herein incorporated by this reference in their entireties. All publications, patents, patent applications, databases and other references cited in this application, all related applications referenced herein, and all references cited therein, are incorporated by reference in their entirety as if restated here in full and as if each individual publication, patent, patent application, database or other reference were specifically and individually indicated to be incorporated by reference.

BACKGROUND OF THE INVENTION

Xanthorrhizol has been shown to possess anticancer, antimicrobial, anti-inflammatory, antioxidant, antihyperglycemic, antihypertensive, nephroprotective, hepatoprotective and neuroprotective activities. Its anticancer activities have been shown in breast, cervical and colon cancers, but not in melanoma or prostate cancers. Mechanisms of action for the anticancer property of xanthorrhizol include cell cycle arrest, apoptosis, upregulation of p53, and anti-metastasis (Itokawa, Hirayama et al. 1985; Choi, Kim et al. 2005; Ismail, Pihie et al. 2005; Cheah, Azimahtol et al. 2006; Cheah, Nordin et al. 2008; Cheah, Nordin et al. 2009; Kang, Park et al. 2009).

Xanthorrhizol belongs to a broad class of isoprenoids, products of plant secondary metabolism. Isoprenoids have been reported to suppress the mevalonate pathway that provides essential intermediates for the posttranslational modification and membrane anchorage of growth-related proteins, including nuclear lamins and Ras (Mo and Elson 2004). Suppression of the mevalonate pathway is mostly attributed to the isoprenoid-mediated downregulation of 3-hydroxy-3-methylglutaryl coenzyme A (HMG CoA) reductase, the rate-limiting enzyme. Consequent to HMG CoA reductase downregulation and mevalonate deprivation, cell cycle arrest and apoptosis occur (Katuru, Fernandes et al. 2011; Fernandes, Yeganehjoo et al. 2013). In additional to early work showing the mevalonate-suppressive activity of monoterpenes, the diterpene geranylgeraniol (Sever, Song et al. 2003; Fernandes, Yeganehjoo et al. 2013) has shown to accelerate the degradation of HMG CoA reductase activity. Other sesquiterpenes including farnesol, β-ionone, and cacalol have shown anti-cancer activities. Xanthorrhizol is available as a synthetic product, as well as, isolated from an essential oil extracted from the rhizomes of *Curcuma xanthorrhiza*.

Tocotrienols, vitamin E molecules with an unsaturated isoprenoid side chain, have been extensively reviewed for their anticancer property (Mo and Elson 2008; Mo, Elfakhani et al. 2013). Tocotrienols at physiologically attainable concentrations suppress the proliferation of tumor cells derived from breast, liver, prostate, skin, pancreas, ovary, colon, blood, lung, lymph gland, cervix, and nerve. Tocotrienol-mediated growth suppression is attributed to cell cycle arrest, mostly at the G1 phase of cell cycle, and apoptosis. Signaling pathways associated with promoting cell cycle progression, growth, and survival, including mitogen-activated protein kinases (MAPK), Ras, RhoA, Raf/MAPK kinase (MEK)/extracellular signal-regulated kinases (ERK), c-Jun, c-myc, cyclin D/cdk4, protein kinase C (PKC), phosphatidylinositol 3-kinase (PI3K), Akt, Iκ B kinase (IKK), Iκ B, nuclear factor κ B (NFK B), c-Jun N-terminal kinase (JNK), Bcl-2, Bcl-xL, COX-2, matrix metalloproteinases (MMP), vascular endothelial growth factor (VEGF), FLIP, and telomerase, are suppressed by tocotrienols. On the other hand, signaling activities supporting growth arrest and apoptosis, including p21cip1WAF1, transforming growth factor-β (TGF-β), p53, Fas, Bax, Apaf-1, caspases, and Bid fragmentation, are activated by tocotrienols. Animal models with chemically initiated carcinogenesis and implanted tumors confirmed the in vitro tumor-suppressive activity of tocotrienols (Mo and Elson 2008). Differing from statins, the nondiscriminant competitive inhibitors of HMG CoA reductase, tocotrienols are discriminant downregulators of the activity of HMG CoA reductase by accelerating its degradation (Song and DeBose-Boyd 2006). Dysregulation of HMG CoA reductase in tumors offers an unique target for malignant intervention. Recent literature continues to support the potential of tocotrienols as tumor-targeted agents in cancer chemoprevention and/or therapy.

Tocotrienols and a number of isoprenoids have shown synergistic effects in growth suppression of tumors. Blends of tocotrienol and geranylgeraniol synergistically suppressed the growth of murine B16 melanoma cells (Katuru, Fernandes et al. 2011) and human DU145 prostate carcinoma cells (Yeganehjoo, DeBose-Boyd et al. 2017). Blends of tocotrienol and β-ionone synergistically suppressed the growth of murine B16 melanoma cells (Mo and Elson 1999); dietary γ-tocotrienol and β-ionone administered individually or together also improved survival in mice bearing implanted melanomas (He, Mo et al. 1997).

BRIEF SUMMARY OF INVENTION

Xanthorrhizol and vitamin E tocotrienol synergistically suppress the proliferation of tumor cells in prostate carcinoma and melanoma, known to respond to tocotrienol but hitherto unknown to respond to xanthorrhizol.

A synergistic dietary supplement composition is disclosed that provides additive and synergistic effects in compositions of tocotrienol:xanthorrhizol in the range of 10:1 to 1:10. This dietary supplement combination provides benefits to individuals consuming it on a regular or periodic basis. The present composition includes one or more isomers of tocotrienol, and xanthorrhizol.

Definitions and Methods

Tocopherol and Tocotrienol: Tocochromanol is collectively known as vitamin E. Vitamin E is a family of two major subgroups, tocopherol and tocotrienol, with each subgroup containing four similar molecules (alpha (α)-, beta (β)-, gamma (γ)-, delta (δ)-tocopherols and (alpha (α)-, beta (β)-, gamma (γ)-, delta (δ) tocotrienols). While nuances in the head structure destine a vitamin E molecule to be an (alpha (α)-, beta (β)-, gamma (γ)-, delta (δ)-form, the length of the molecule's tail determines whether a vitamin E molecule belongs to the tocopherol or tocotrienol subfamily. Tocotrienols are more flexible with a shorter unsaturated tail, while tocopherols have a longer saturated tail and are less flexible.

*Curcuma xanthorrhiza* Roxb. (*C. xanthorrhiza* D. Dietrich), rhizome: It belongs to the ginger family named Zingiberaceae. There were two classes of characteristic constituents, curcuminoids and volatile oil in the root of *Curcuma xanthorrhiza*. Curcuminoids are 1-2% containing curcumin powder, its derivatives and others. Volatile oil is around 3-12%, composed mainly of xanthorrizol (44.5%), curcumene, camphor and others (HMPC 2014).

Xanthorrhizol: It is a sesquiterpenoid isolated from the essential oil extracted from the rhizomes of *Curcuma xanthorrhiza*, a ginger-like plant of the Zingiberaceae family. Originating from the Indonesian island of Java, the plant is often referred to as "Java Ginger" or "Temulawak," and is also cultivated in Malaysia, Thailand, and the Philippines. Research into xanthorrhizol's therapeutic uses suggests that the compound has antimicrobial, anti-inflammatory, antioxidant, antihyperlipidemic, antihypertensive, antiplatelet, nephroprotective, hepatoprotective, estrogenic and antiestrogenic properties (Oon, Nallappan et al. 2015).

*Curcuma longa* (Turmeric) and Turmerone: *Curcuma longa* also belongs to the ginger family named Zingiberaceae. Commercially, curcumin powder on the market is extracted from *Curcuma longa*. Turmerone is isolated from the essential oil extracted *Curcuma longa* root. Usually, *Curcuma longa* yields to 4-5% of turmeric oil, composed mainly of turmerones (60%).

Synergism: When two or more compounds or drugs are administered together, they have an interactive effect including synergistic (increased effect), additive or antagonistic effect (decreased effect). Synergism as an interactive effect of the mixed compounds was determined by the isobologram and the Combination Index (CI) calculated using the CompuSyn software. Equipotent plots in FIG. 6 provides visual illustration of synergism, antagonism, or additive effects of the combination of two components. In general, combination data points located on the lower-left and upper-right of their corresponding lines indicate synergism and antagonism, respectively. If the combination data point lies on the corresponding line, the effect is considered additive. Combination index (CI) values lower than 1 indicate synergistic effect of the agents.

Cell Cycle and Cell Cycle Arrest: The cell cycle produces two separate cells by division and duplication of its DNA, which involves four phases, G1, S, G2 and M phase. Cell cycle starts with G1, a preparation step to duplicate itself, and proceeds to S phase to actively synthesize its genetic material, DNA, and G2 phase repairs damage as an interphase, and lastly M phase for mitosis. When a cell is no longer involved in division and duplication, the cell enters into cell cycle arrest, a stopping point in a cell cycle. If a cell senses DNA damage, cell arrest proceeds to apoptosis, programmed cell death. Moreover, G/S ratio is an indicator of cell cycle arrest.

The following terms are used in the description herein and the appended claims: The singular forms "a," "an" and "the" are intended to include the plural forms as well, unless the context clearly indicates otherwise.

Furthermore, the term "about," as used herein when referring to a measurable value such as an amount of the length of a polynucleotide or polypeptide sequence, dose, time, temperature, and the like, is meant to encompass variations of ±20%, ±10%, ±5%, ±1%, ±0.5%, or even ±0.1% of the specified amount.

Also as used herein, "and/or" refers to and encompasses any and all possible combinations of one or more of the associated listed items, as well as the lack of combinations when interpreted in the alternative ("or").

As used herein, the transitional phrase "consisting essentially of" means that the scope of a claim is to be interpreted to encompass the specified materials or steps recited in the claim, "and those that do not materially affect the basic and novel characteristic(s)" of the claimed invention. See, In re Herz, 537 F.2d 549, 551-52, 190 USPQ 461,463 (CCPA 1976) (emphasis in the original); see also MPEP § 2111.03. Thus, the term "consisting essentially of" when used in a claim of this invention is not intended to be interpreted to be equivalent to "comprising." Unless the context indicates otherwise, it is specifically intended that the various features of the invention described herein can be used in any combination.

By the terms "treat," "treating" or "treatment of" (and grammatical variations thereof) it is meant that the severity of the subject's condition is reduced, at least partially improved or stabilized and/or that some alleviation, mitigation, decrease or stabilization in at least one clinical symptom is achieved and/or there is a delay in the progression of the disease or disorder.

A "treatment effective" amount as used herein is an amount that is sufficient to provide some improvement or benefit to the subject. Alternatively stated, a "treatment effective" amount is an amount that will provide some alleviation, mitigation, decrease or stabilization in at least one clinical symptom in the subject. Those skilled in the art will appreciate that the therapeutic effects need not be complete or curative, as long as some benefit is provided to the subject.

BRIEF DESCRIPTION OF DRAWING

FIG. 7. The concentration-dependent effect of blends of xanthorrhizol and d-δ-tocotrienol on the growth of human DU145 prostate carcinoma cells. DU145 cells were incubated with blends of xanthorrhizol (50 and 100 µmol/L) and d-δ-tocotrienol (10 and 20 µmol/L) at a 5:1 concentration ratio. CI values of less than 1 indicate synergism of xanthorrhizol and d-δ-tocotrienol blended in a 5:1 ratio. Values represent the means±SEM, n>3. Values not sharing a common letter are different (P<0.05).

DETAILED DESCRIPTION OF THE INVENTION

Figure 1:
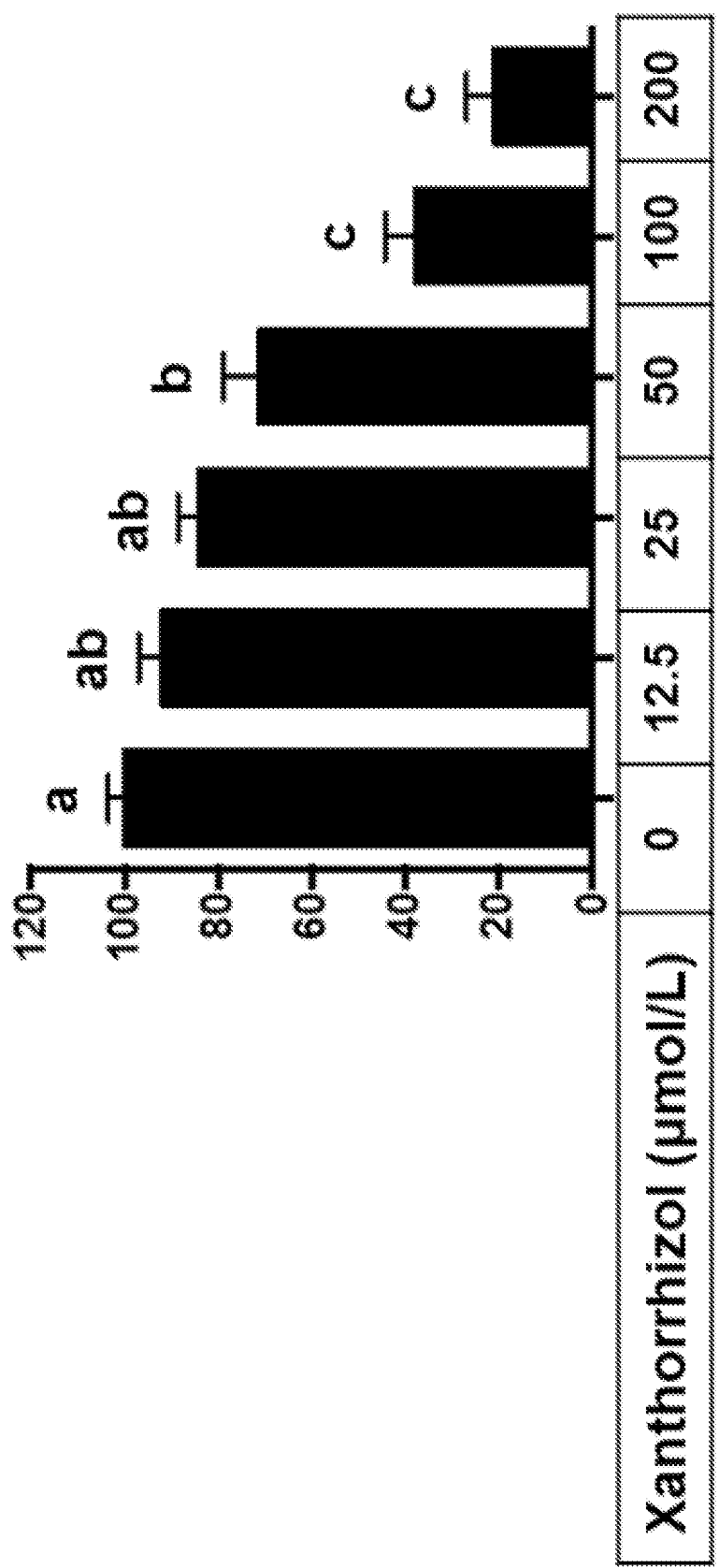
FIG. 1. The effect of xanthorrhizol on the growth of murine B16 melanoma cells. Values represent the means±SEM, n>3. Values not sharing a common letter are different ($P<0.05$).

The mevalonate pathway provides essential intermediates, including farnesyl- and geranylgeranyl-pyrophosphates, for the post-translational modification and biological activity of growth-associated proteins such as RAS. Tocotrienols and other isoprenoids, including the sesquiterpenes, downregulate 3-hydroxy-3-methylglutaryl coenzyme A (HMG CoA) reductase, the rate-limiting enzyme in the mevalonate pathway, and consequently suppress cell growth. Xanthorrhizol is a sesquiterpene shown to suppress tumor cell proliferation. Synergistic effects of delta-tocotrienol (d-δ-tocotrienol) and xanthorrhizol towards the treatment of malignancies are disclosed.

Cell Growth Assay:

Cultures of cells, seeded in 0.1 mL medium with a density of 1,500 DU145 cells/well or 1,200 B16 cells/well in a 96-well plate, were incubated for 24 h at 37° C. in a humidified atmosphere of 5% $CO_2$. At 24 h, the medium was decanted from each well and replaced with 0.1 mL fresh medium containing different concentrations of the test agents. Incubation continued for additional 48 h (B16) or 72 h (DU145). Following a quick rinse with 0.1 mL Hank's Balanced Salt Solution (HBSS), the 48-h (B16) or 72-h (DU145) cell populations were determined by adding 20 µL of CellTiter 96® Aqueous One Solution (Promega, Madison, Wis.) to each well; plates were held in the dark at 37° C. for 2 h and then read with a Synergy HT multi-plate reader (Biotek Instruments, Inc., Winooski, Vt.) and analyzed using the Gen5™ software (Biotek Instruments, Inc.). Absorbances from wells containing cell-free medium were used as baselines and were deducted from those of other cell-containing wells. The $IC_{50}$ value is the concentration of xanthorrhizol required to suppress the net increase in cell number by 50%.

Cell Cycle Analysis:

Cells were seeded in 25 $cm^2$ flasks (Becton Dickinson Labware, Franklin Lakes, N.J.) at $1\times10^6$ cells (B16) per flask with 3 mL medium/flask and incubated for 24 h. Medium was then decanted and cultures were replenished with fresh medium containing the test agents that had been dissolved in ethyl alcohol. Following an additional 24-h incubation, adherent cells were harvested by trypsinization and pelleted by low speed centrifugation at 500 g for 5 min. Cell pellets were gently fixed in 1 mL of 70% ethanol-PBS mixture at −20° C. overnight and washed with PBS before $5\times10^5$ cells were re-suspended in 500 µL of PBS containing freshly prepared propidium iodide and RNase A (Roche Diagnostics, Indianapolis, Ind.) and incubated at 37° C. in the dark for 30 min as described (Yeganehjoo, DeBose-Boyd et al. 2017). Aliquots of 200 µL of the stained cells were analyzed for DNA content using a BD LSR Fortessa flow cytometer (BD Biosciences, San Jose, Calif.). The distribution of cells in the G1 and S phases of the cell cycle was determined using MultiCycle AV software (Phoenix Flow Systems, San Diego, Calif.).

Statistics:

One-way analysis of variance (ANOVA) and Kruskal-Wallis tests were performed to assess the differences between groups using Prism® 7.0 software (GraphPad Software Inc., San Diego, Calif.). Differences in means were analyzed by Dunnett's multiple comparison test unless specified otherwise. Values were mean±standard error of mean (SEM). Levels of significance were designated as P<0.05. Isobologram and combination index (CI) based on the CompuSyn software (ComboSyn, Inc., Paramus, N.J.) were used to demonstrate the synergistic anti-proliferative impacts of combinations of xanthorrhizol and d-δ-tocotrienol. The constant-ratio combination design of xanthorrhizol and d-δ-tocotrienol in our study allowed automated creation of the classic isobologram by using the CompuSyn software. CI values lower than 1 indicate synergistic effect of the agents (Tallarida 2006).

Example 1

Murine B16 melanoma cells were cultured in Dulbecco's Modified Eagle's Medium (DMEM) supplemented with 10% FBS, 1% penicillin-streptomycin and 0.8% gentamicin. For optimal growth, cells were incubated at 37° C. in a humidified atmosphere of 5% $CO_2$. d-δ-Tocotrienol and xanthorrhizol were pre-dissolved in ethyl alcohol. All treated cultures contained 0.1% (v/v) of ethyl alcohol.

Figure 2:
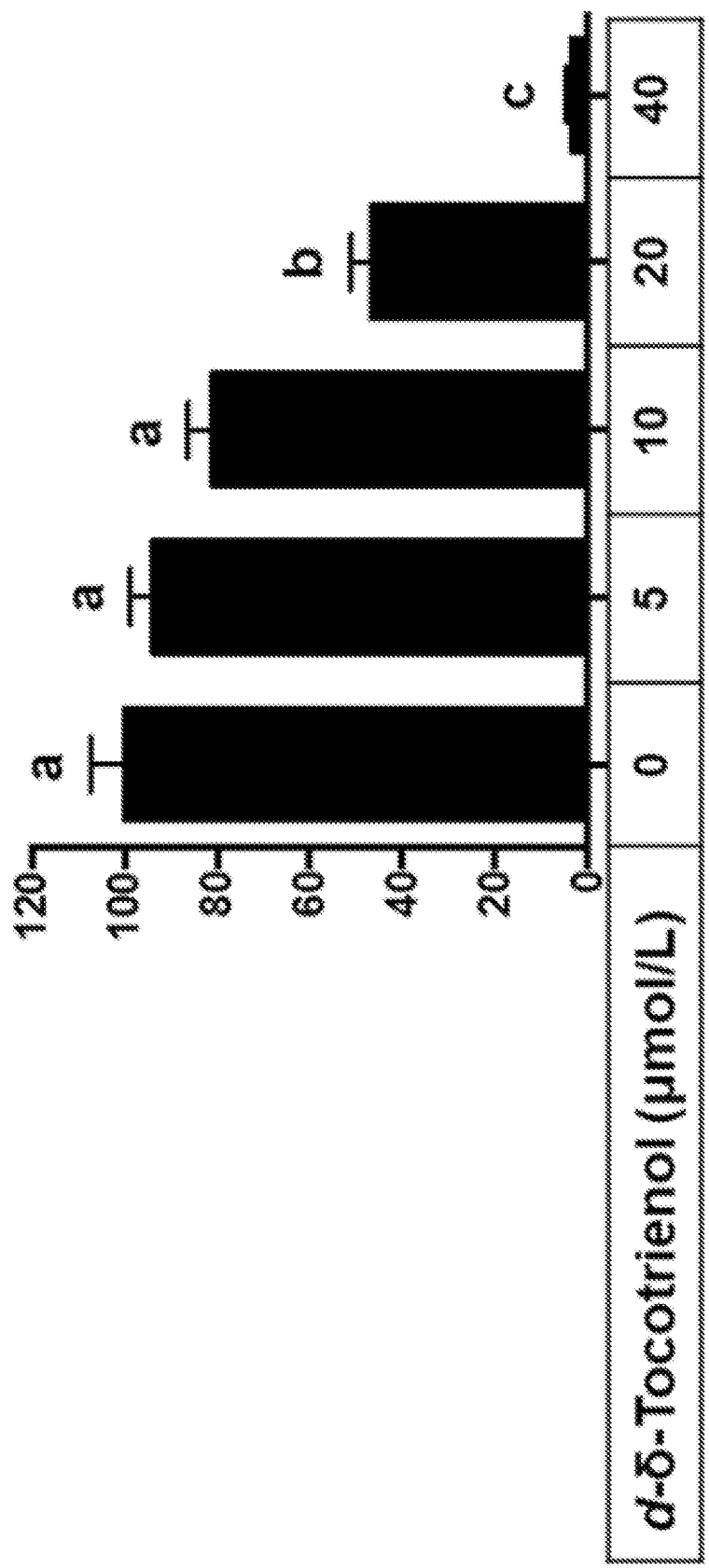
FIG. 2. The effect of d-δ-tocotrienol on the growth of murine B16 melanoma cells. Values represent the means±SEM, n>3. Values not sharing a common letter are different ($P<0.05$).
Figure 3:
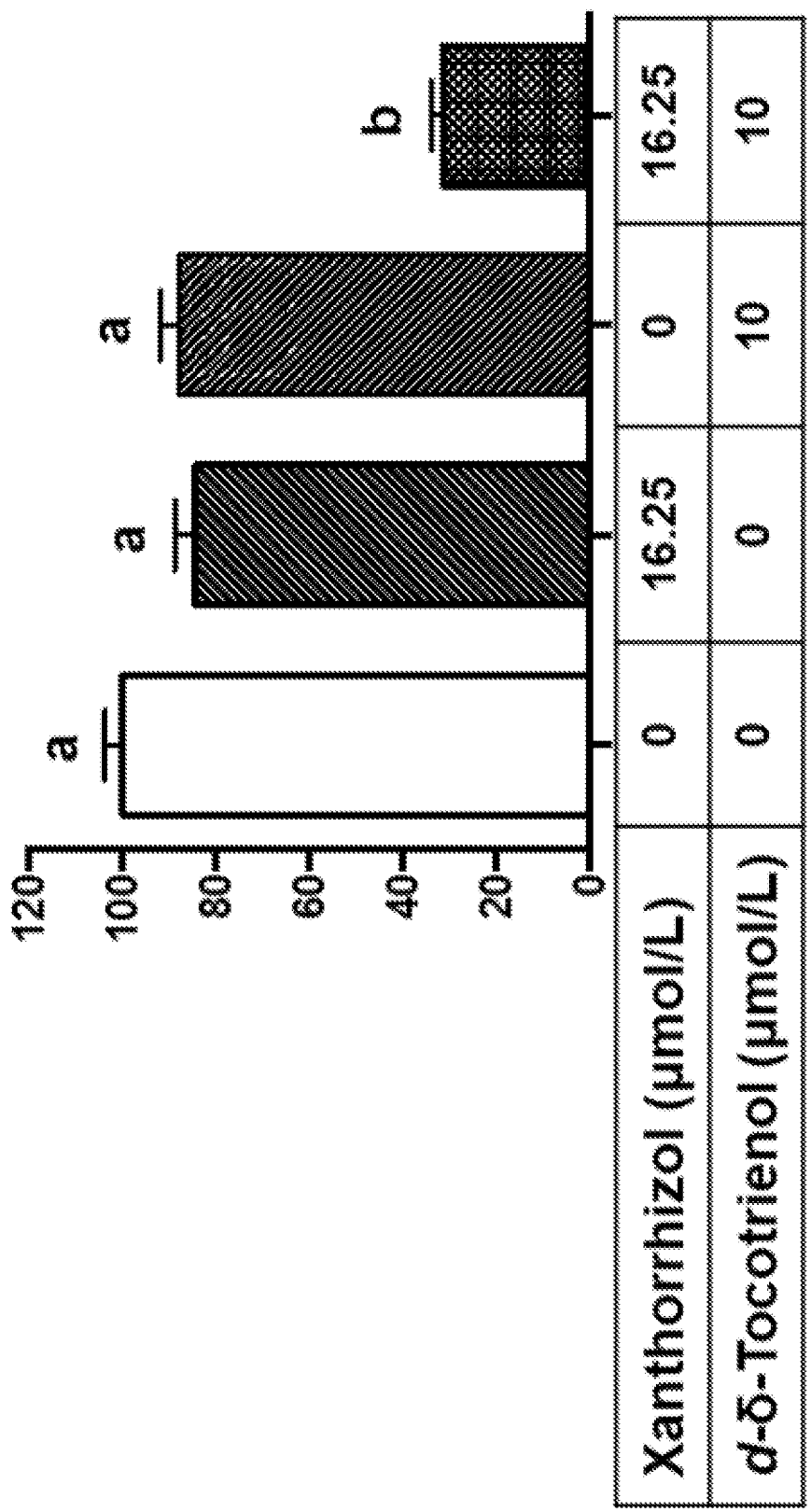
FIG. 3. The synergistic effect of xanthorrhizol and d-δ-tocotrienol on the growth of murine B16 melanoma cells. Values represent the means±SEM, n>3. Values not sharing a common letter are different ($P<0.05$).

Xanthorrhizol (0-200 µmol/L) and d-δ-tocotrienol (0-40 µmol/L) each elicited a concentration-dependent suppression of the proliferation of murine B16 melanoma cells (FIGS. 1 & 2). B16 cells were more sensitive to the growth suppression induced by d-δ-tocotrienol—with a potency consistent with a previous reported IC50, the concentration required to elicit 50% of growth inhibition, of 14 µmol/L (McAnally, Gupta et al. 2007)—than that induced by xanthorrhizol (IC50=65 µmol/L). The potency of IC50 for d-δ-tocotrienol to xanthorrhizol is approximately 5:1. When applied individually, 16.25 µmol/L xanthorrhizol and 10 µmol/L d-δ-tocotrienol suppressed the growth of B16 cells by approximately 15% (P>0.05) and 12% (P>0.05), respectively. A blend of 16.25 µmol/L of xanthorrhizol and 10 µmol/L of d-δ-tocotrienol achieved 69% (P<0.05) growth suppression, exceeding the sum of individual effects (FIG. 3).

Example 2

Figure 4:
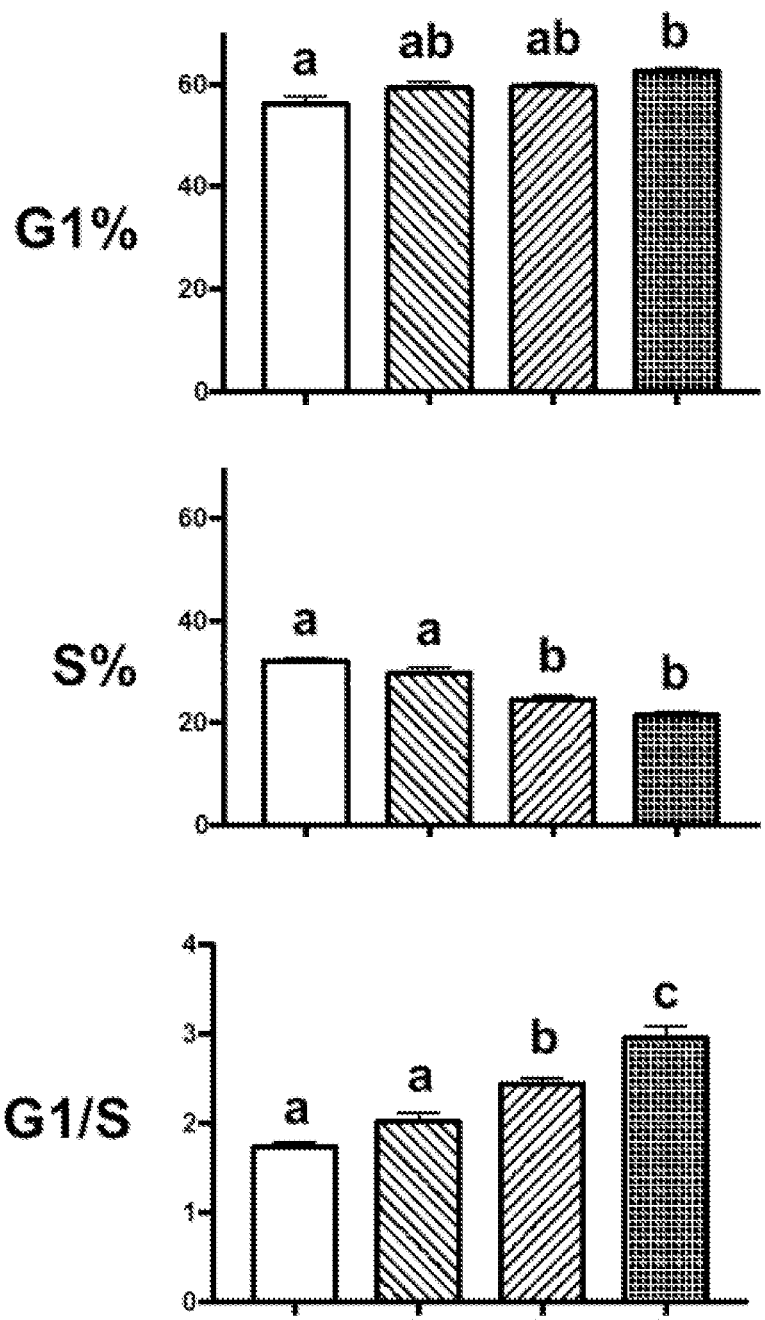
FIG. 4. The effect of d-δ-tocotrienol and xanthorrhizol on the 24-hour cell cycle distribution of murine B16 melanoma cells. Samples were analyzed for DNA content by flow cytometry. The percentages of B16 cells in the G1 and S phases of the cell cycle following 24-hour incubations with the agents are shown. The G1/S ratio of B16 cells at 24-hour shows the cumulative effect of d-δ-tocotrienol and xanthorrhizol. Values are means±SEM, n≥6. Values not sharing a common letter are different ($P<0.05$).

The effect of blends of xanthorrhizol and d-δ-tocotrienol were evaluated on the cell cycle distribution of murine B16 melanoma cells (FIG. 4). At 0-h as baseline, the percentages of cells in the G1, S, and G2 phases of cell cycle were 54.1±0.7%, 27.6±0.4%, and 18.3±0.8% (mean±SEM), respectively. Following a 24-h incubation as baseline, these percentages were relatively stable for the control group (56.1±1.6%, 32.1±0.6% and 11.7±1.9% for G1, S and G2 phases, respectively).

Xanthorrhizol and d-δ-tocotrienol had a cumulative effect on cell cycle distribution (FIG. 4). B16 cells incubated with 5 µmol/L d-δ-tocotrienol (59.2±1.3%) [second column of G1 of FIG. 4] and 16.25 µmol/L xanthorrhizol (59.5±0.7%) [third column of G1 of FIG. 4] for 24-h had no significant changes in the percentages of cells at the G1 phase. A blend of 5 µmol/L d-δ-tocotrienol and 16.25 µmol/L xanthorrhizol increased the percentage of cells in the G1 phase to 62.6±0.6% [fourth column of G1 of FIG. 4], a significant increase over that of the control group (56.1±1.6%) [first column of G1 of FIG. 4], suggesting a synergism consistent with the growth suppression shown in FIG. 3. Conversely, the percentage of cells at the S phase decreased in the xanthorrhizol and combination groups. Additionally, the xanthorrhizol and combination groups had significantly higher G1/S ratios, an indicator of cell cycle arrest, confirming their cumulative effect on G1 arrest.

Therefore, the synergism shown in FIG. 4 is consistent with FIG. 3. FIG. 4 shows the mechanism demonstrated in FIG. 3.

Example 3

Human DU145 prostate carcinoma cells were cultured in Roswell Park Memorial Institute (RPMI-1460) medium supplemented with 10% Fetal Bovine Serum (FBS; Fisher Scientific, Houston, Tex.), 1% penicillin-streptomycin (Fisher Scientific), and 0.8% gentamicin (Fisher Scientific).

Figure 5:
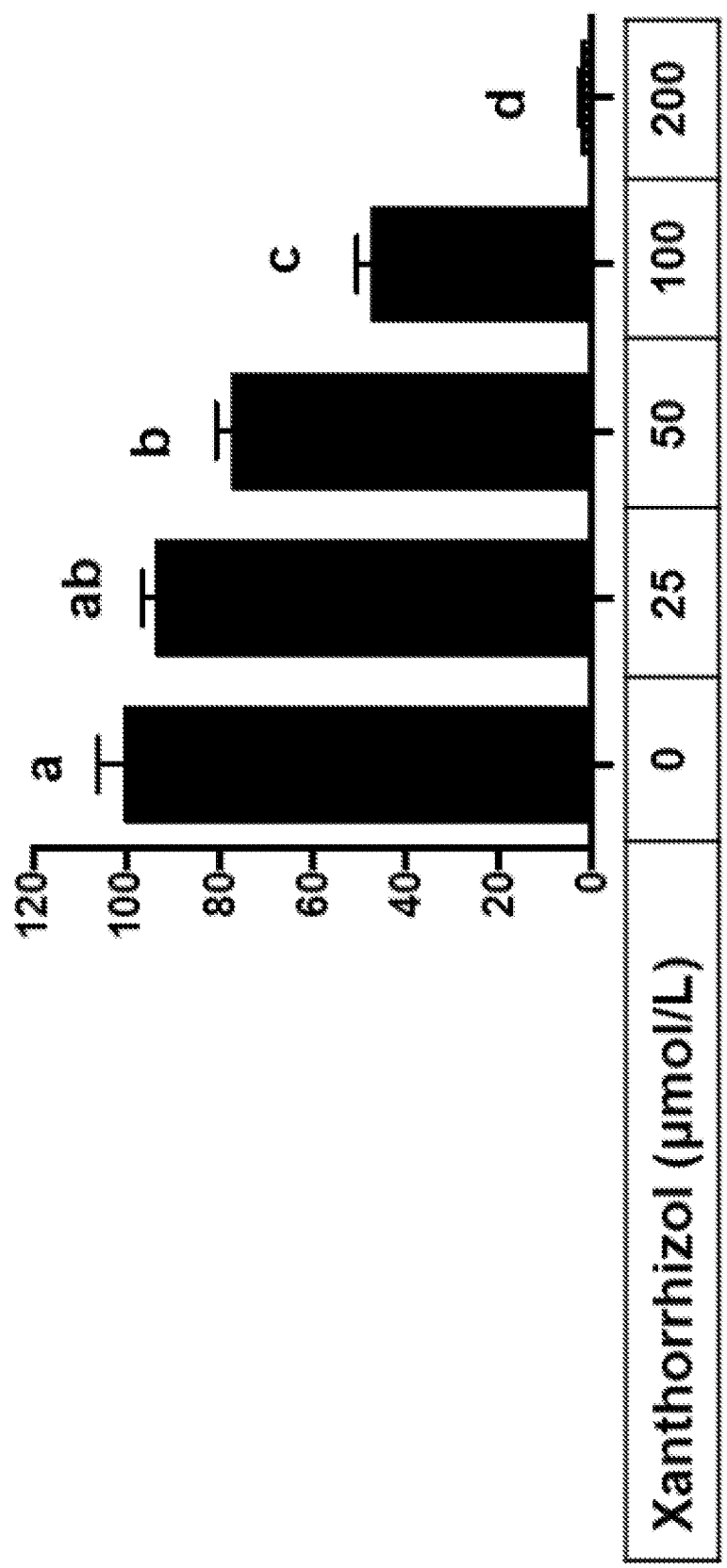
FIG. 5. The concentration-dependent effect of xanthorrhizol on the growth of human DU145 prostate carcinoma cells. Values represent the means±SEM, n>3. Values not sharing a common letter are different ($P<0.05$).
Figure 6:
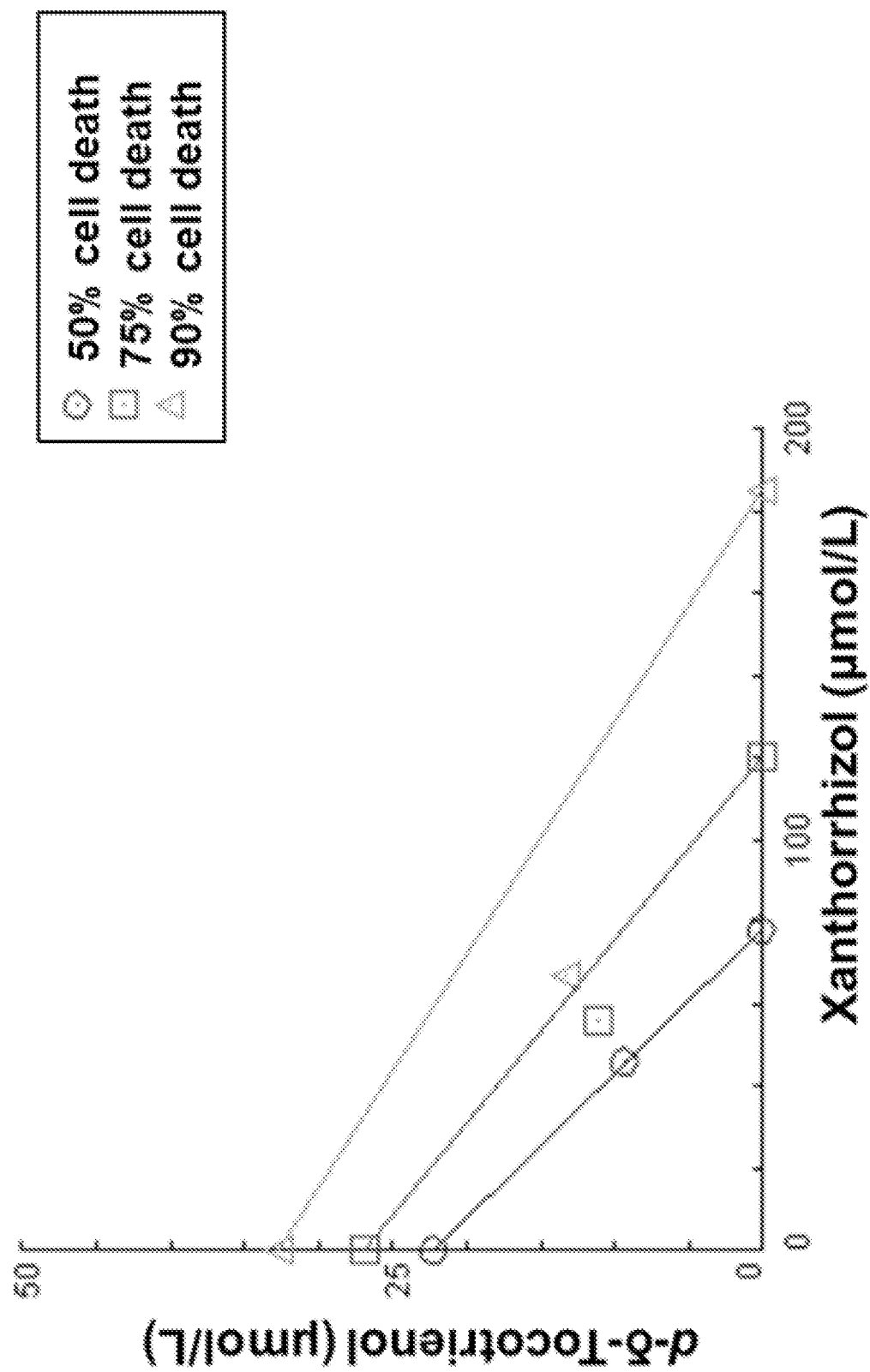
FIG. 6. The concentration-dependent effect of blends of xanthorrhizol and d-δ-tocotrienol on the growth of human DU145 prostate carcinoma cells. DU145 cells were incubated with blends of xanthorrhizol and d-δ-tocotrienol. Circles, rectangles, and triangles depict 50%, 75%, and 90% growth inhibitions achieved by the individual and combined test agents, respectively; data points located on the axes represent the individual agents. Data points for the combinations located on the lower-left of their corresponding lines shown by identical shapes indicate synergistic effects of the two agents. Values represent the means±SEM, n>3. Values not sharing a common letter are different ($P<0.05$).

Xanthorrhizol (0-200 μmol/L) induced a concentration-dependent suppression of the proliferation of human DU145 prostate carcinoma cells (FIG. 5) with an IC50 of 101 μmol/L. DU145 cells were incubated with blends of xanthorrhizol and d-δ-tocotrienol. In general, combination data points located on the lower-left and upper-right of their corresponding lines indicate synergism and antagonism, respectively (FIG. 6). If the combination data point lies on the corresponding line, the effect is considered additive (FIG. 6). In FIG. 6, 90% of growth suppression was achieved by 182 μmol/L xanthorrhizol and 32 μmol/L d-δ-tocotrienol, respectively, in DU145 cells. The same 90% growth suppression was achieved by a blend of 62 μmol/L xanthorrhizol and 18 μmol/L d-δ-tocotrienol (3.4:1) and, a data point (triangle in the quadrant) located on the lower-left of the upper right line, indicating synergistic impact of the two agents. By the same measure, the data point for 75% growth suppression achieved by a blend of these two agents (square) is located on the lower-left of the middle line, again indicating synergism. The data point for 50% growth suppression achieved by a blend (circle) is located on the line, indicating an additive effect. DU145 cells were incubated with blends of xanthorrhizol (50 and 100 μmol/L) and d-δ-tocotrienol (10 and 20 μmol/L) at a 5:1 concentration ratio. The CI values of 0.94 and 0.61 for a total dose of 60 and 120 μmol/L, respectively, further confirmed synergy (FIG. 7).

Embodiments

In an embodiment, synergistic effects of xanthorrhizol and tocotrienol on melanoma were seen at ratios of xanthorrhizol:tocotrienol at 1.6:1 to 3.3:1.

In an embodiment, synergistic effects of xanthorrhizol and tocotrienol on prostate cancer were seen at ratios of xanthorrhizol and tocotrienol at 3.4 to 5:1.

In an embodiment, a dietary supplement composition provided synergistic effects of xanthorrhizol and tocotrienol on malignancies.

In an embodiment, synergistic effects of xanthorrhizol and tocotrienol on melanoma.

In an embodiment, a blend of xanthorrhizol and delta tocotrienol achieved growth suppression of melanoma, which exceeded the sum of individual effects. In an embodiment, a blend of xanthorrhizol and delta tocotrienol achieved at least 69% growth suppression of melanoma, which exceeded the sum of individual effects.

In an embodiment, synergistic effects of xanthorrhizol and tocotrienol on melanoma.

In an embodiment, a blend of xanthorrhizol and delta tocotrienol achieved 90% growth suppression in prostate cancer.

In an embodiment, 90% of growth suppression was achieved by 3-fold xanthorrhizol and 1.8-fold delta tocotrienol respectively, which indicated synergistic impact of the two agents.

In an embodiment, mechanisms of action for the anticancer property showed synergism of xanthorrhizol and tocotrienol-mediated cancer growth suppression was attributed to cell cycle arrest at the G1 phase of cell cycle, and apoptosis.

In an embodiment, novel dietary supplement combination of xanthorrhizol to tocotrienol (1:1 to 10:1) may provide benefits to individuals consuming it on a regular or periodic basis.

In an embodiment, a mixture of xanthorrhizol (including curcumenes, turmerones and curcumins) and vitamin E (tocochromanols) is synergistic for biological benefits.

In an embodiment, ratio of tocotrienol to xanthorrhizol is 1:1 to 1:10 for synergistic effects.

In an embodiment, tocochromanol is selected from delta-tocotrienol, gamma-tocotrienol and alpha-tocotrienol.

In an embodiment, tocochromanol is a mixture of one or more tocotrienol isomers.

In an embodiment, *Curcuma* terpenoid is selected from xanthorrhizol, curcumenes, terpenoids or a mixture of one or more *Curcuma* terpenoids.

In an embodiment, xanthorrhizol and geranylgeraniol are synergistic.

In an embodiment, a mixture of xanthorrhizol, geranylgeraniol and tocotrienol is synergistic.

In an embodiment, the biological benefits of compositions of a mixture of xanthorrhizol and geranylgeraniol; a mixture of xanthorrhizol, geranylgeraniol and tocotrienol; and a mixture of xanthorrhizol and tocochromanol apply to malignancies, metabolic syndrome, and inflammation.

In an embodiment, more than one administration (e.g., two, three, four, five, six, seven, eight, nine, ten, etc., or more administrations) may be employed.

In an embodiment, to achieve the desired effect, administration can be over a period of various intervals, e.g., hourly, daily, weekly, monthly, yearly, etc.

In an embodiment, dosing can be single dosage or cumulative (serial dosing), and can be readily determined by one skilled in the art.

In an embodiment, treatment may comprise multiple administrations of an effective dose over a range of time periods, such as, e.g., once daily, twice daily, trice daily, once every few days, or once weekly.

In an embodiment, the timing of administration can vary from individual to individual, depending upon such factors as the severity of an individual's symptoms.

In an embodiment, the period of administration is for 1 day, 2 days, 3 days, 4 days, 5 days, 6 days, 7 days, 8 days, 9 days, 10 days, 11 days, 12 days, 13 days, 14 days, 3 weeks, 4 weeks, 5 weeks, 6 weeks, 7 weeks, 8 weeks, 9 weeks, 10 weeks, 11 weeks, 12 weeks, 4 months, 5 months, 6 months, 7 months, 8 months, 9 months, 10 months, 11 months, 12 months, or more. In a further embodiment, a period during which administration is stopped is for 1 day, 2 days, 3 days, 4 days, 5 days, 6 days, 7 days, 8 days, 9 days, 10 days, 11 days, 12 days, 13 days, 14 days, 3 weeks, 4 weeks, 5 weeks, 6 weeks, 7 weeks, 8 weeks, 9 weeks, 10 weeks, 11 weeks, 12 weeks, 4 months, 5 months, 6 months, 7 months, 8 months, 9 months, 10 months, 11 months, 12 months, or more.

In an embodiment, exemplary modes of administration include oral, rectal, transmucosal, parenteral (e.g., intravenous, subcutaneous, intradermal, intramuscular, intradermal, topical. Administration can also be to a tumor (e.g., in or near a tumor or a lymph node). The most suitable route in any given case will depend on the nature and severity of the condition being treated and/or prevented.

In an embodiment, the composition reduces the severity by, e.g., at least 10%, at least 15%, at least 20%, at least 25%, at least 30%, at least 35%, at least 40%, at least 45%, at least 50%, at least 55%, at least 60%, at least 65%, at least 70%, at least 75%, at least 80%, at least 85%, at least 90% or at least 95%.

In an embodiment, the composition reduces the severity from, e.g., about 5% to about 100%, about 10% to about 100%, about 20% to about 100%, about 30% to about 100%, about 40% to about 100%, about 50% to about 100%, about 60% to about 100%, about 70% to about 100%, about 80% to about 100%, about 10% to about 90%, about 20% to about 90%, about 30% to about 90%, about 40% to about 90%, about 50% to about 90%, about 60% to about 90%, about 70% to about 90%, about 10% to about 80%, about 20% to about 80%, about 30% to about 80%, about 40% to about 80%, about 50% to about 80%, or about 60% to about 80%, about 10% to about 70%, about 20% to about 70%, about 30% to about 700%, about 40% to about 70%, or about 50% to about 70%.

In an embodiment, the present specification discloses, in part, treating an individual.

In an embodiment, the term "treating" can mean reducing a symptom of a condition characterized by a disease or disorder, by, e.g., at least 20%, at least 25%, at least 30%, at least 35%, at least 40%, at least 45%, at least 50%, at least 55%, at least 60%, at least 65%, at least 70%, at least 75%, at least 80%, at least 85%, at least 90% at least 95%, or at least 100%. The actual symptoms associated with a specific disease or disorder are well known and can be determined by a person of ordinary skill in the art by taking into account factors, including, without limitation, the location of the disease or disorder, the cause of the disease or disorder, the severity of the disease or disorder, and/or the tissue or organ affected by the disease or disorder. Those of skill in the art will know the appropriate symptoms or indicators associated with a specific type of disease or disorder and will know how to determine if an individual is a candidate for treatment as disclosed herein.

In an embodiment, a therapeutically effective amount disclosed herein reduces a symptom associated with a disease or disorder by, e.g., at least 10%, at least 15%, at least 20%, at least 25%, at least 30%, at least 35%, at least 40%, at least 45%, at least 50%, at least 55%, at least 60%, at least 65%, at least 70%, at least 75%, at least 80%, at least 85%, at least 90%, at least 95% or at least 100%.

In an embodiment, a therapeutically effective amount of a composition of xanthorrhizol and tocochromanol disclosed herein reduces a symptom associated with a disease or disorder by, e.g., at most 10%, at most 15%, at most 20%, at most 25%, at most 30%, at most 35%, at most 40%, at most 45%, at most 50%, at most 55%, at most 60%, at most 65%, at most 70%, at most 75%, at most 80%, at most 85%, at most 90%, at most 95% or at most 100%.

In an embodiment, a therapeutically effective amount of a composition of xanthorrhizol and tocochromanol herein reduces a symptom associated with disease or disorder by, e.g., about 10% to about 100%, about 10% to about 90%, about 10% to about 80%, about 10% to about 70%, about 10% to about 60%, about 10% to about 50%, about 10% to about 40%, about 20% to about 100%, about 20% to about 90%, about 20% to about 80%, about 20% to about 20%, about 20% to about 60%, about 20% to about 50%, about 20% to about 40%, about 30% to about 100%, about 30% to about 90%, about 30% to about 80%, about 30% to about 70%, about 30% to about 60%, or about 30% to about 50%.

In an embodiment, a composition of xanthorrhizol and tocochromanol is capable of reducing the severity of a disease or disorder in an individual suffering from the disease or disorder by, e.g., about 10% to about 100%, about 20% to about 100%, about 30% to about 100%, about 40% to about 100%, about 50% to about 100%, about 60% to about 100%, about 70% to about 100%, about 80% to about 100%, about 10% to about 90%, about 20% to about 90%, about 30% to about 90%, about 40% to about 90%, about 50% to about 90%, about 60% to about 90%, about 70% to about 90%, about 10% to about 80%, about 20% to about 80%, about 30% to about 80%, about 40% to about 80%, about 50% to about 80%, or about 60% to about 80%, about 10% to about 70%, about 20% to about 70%, about 30% to about 70%, about 40% to about 70%, or about 50% to about 70% as compared to a patient not receiving the same treatment.

In an embodiment, a therapeutically effective amount of a composition of xanthorrhizol and tocochromanol disclosed herein reduces the severity of a disease or disorder or maintains the severity of a disease or disorder in an individual by, e.g., at most 10%, at most 15%, at most 20%, at most 25%, at most 30%, at most 35%, at most 40%, at most 45%, at most 50%, at most 55%, at most 60%, at most 65%, at most 70%, at most 75%, at most 80%, at most 85%, at most 90%, at most 95% or at most 100%.

In an embodiment, a therapeutically effective amount of a composition of xanthorrhizol and tocochromanol disclosed herein reduces or maintains the severity of a disease or disorder in an individual by, e.g., about 10% to about 100%, about 10% to about 90%, about 10% to about 80%, about 10% to about 70%, about 10% to about 60%, about 10% to about 50%, about 10% to about 40%, about 20% to about 100%, about 20% to about 90%, about 20% to about 80%, about 20% to about 20%, about 20% to about 60%, about 20% to about 50%, about 20% to about 40%, about 30% to about 100%, about 30% to about 90%, about 30% to about 80%, about 30% to about 70%, about 30% to about 60%, or about 30% to about 50%.

Paragraph 1. A method of treatment, comprising orally administering a composition of xanthorrhizol and tocochromanol; wherein the composition has ratio of xanthorrhizol:tocochromanol from 1:10 to 10:1.

Paragraph 2. The method of Paragraph 1, further comprising a geranylgeraniol.

Paragraph 3. The method of Paragraph 1, wherein the tocochromanol is a tocotrienol.

Paragraph 4. The method of Paragraph 3, wherein the tocotrienol is an isomer of tocotrienol.

Paragraph 5. The method of Paragraph 4, wherein the isomer of tocotrienol is δ-tocotrienol.

Paragraph 6. The method of Paragraph 4, wherein the isomer of tocotrienol is γ-tocotrienol.

Paragraph 7. The method of Paragraph 1, wherein the tocochromanol is a tocopherol.

Paragraph 8. The method of Paragraph 1, wherein the tocochromanol is a synthetic tocochromanol.

Paragraph 9. The method of Paragraph 1, wherein the tocochromanol is a natural tocochromanol.

Paragraph 10. The method of Paragraph 3, wherein the tocotrienol is a natural tocotrienol.

Paragraph 11. The method of Paragraph 7, wherein the tocopherol is a natural tocopherol.

Paragraph 12. The method of Paragraph 1, wherein the xanthorrhizol is a synthetic xanthorrhizol.

Paragraph 13. The method of Paragraph 1, wherein the xanthorrhizol is a natural xanthorrhizol.

Paragraph 14. The method of Paragraph 1, wherein the composition has an effect with an Combination Index (CI) value lower than 1.

Paragraph 15. The method of Paragraph 2, wherein the composition has an effect with an Combination Index (CI) value lower than 1.

Paragraph 16. The method of Paragraph 1, wherein the tocochromanol is a mixture of one or more tocotrienol isomers.

Paragraph 17. A method of treatment, comprising orally administering a composition of *Curcuma* terpenoid and tocochromanol; wherein the composition has ratio of *Curcuma* terpenoid:tocochromanol from 1:10 to 10:1.

Paragraph 18. The method of Paragraph 17, wherein the *Curcuma* terpenoid is selected from the group consisting of xanthorrhizol, curcumene, turmerone, curcumin and mixtures thereof.

Paragraph 19. A method of treatment, comprising orally administering a composition of *Curcuma* terpenoid and geranylgeraniol; wherein the composition has ratio of *Curcuma* terpenoid:geranylgeraniol from 1:10 to 10:1.

REFERENCES

Cheah, Y. H., H. L. Azimahtol, et al. (2006). "Xanthorrhizol exhibits antiproliferative activity on MCF-7 breast cancer cells via apoptosis induction." Anticancer Res 26(6B): 4527-4534.

Cheah, Y. H., F. J. Nordin, et al. (2009). "Combined xanthorrhizol-curcumin exhibits synergistic growth inhibitory activity via apoptosis induction in human breast cancer cells MDA-MB-231." Cancer Cell Int 9: 1.

Cheah, Y. H., F. J. Nordin, et al. (2008). "Antiproliferative property and apoptotic effect of xanthorrhizol on MDA-MB-231 breast cancer cells." Anticancer Res 28(6A): 3677-3689.

Choi, M. A., S. H. Kim, et al. (2005). "Xanthorrhizol, a natural sesquiterpenoid from *Curcuma xanthorrhiza*, has an anti-metastatic potential in experimental mouse lung metastasis model." Biochem Biophys Res Commun 326(1): 210-217.

Fernandes, N. V., H. Yeganehjoo, et al. (2013). "Geranylgeraniol suppresses the viability of human DU145 prostate carcinoma cells and the level of HMG CoA reductase." Exp Biol Med (Maywood) 238(11): 1265-1274.

He, L., H. Mo, et al. (1997). "Isoprenoids suppress the growth of murine B16 melanomas in vitro and in vivo." J Nutr 127(5): 668-674.

HMPC, E. m. a. C. o. H. M. P. E. m. a. (2014). Assessment report on *Curcuma xanthorrhiza* Roxb. (*C. xanthorrhiza* D. Dietrich), rhizoma. E. m. agency. 28 January.

Ismail, N., A. H. Pihie, et al. (2005). "Xanthorrhizol induces apoptosis via the upregulation of bax and p53 in HeLa cells." Anticancer Res 25(3B): 2221-2227.

Itokawa, H., F. Hirayama, et al. (1985). "Studies on the antitumor bisabolane sesquiterpenoids isolated from *Curcuma xanthorrhiza*." Chem Pharm Bull (Tokyo) 33(8): 3488-3492.

Kang, Y. J., K. K. Park, et al. (2009). "Xanthorrhizol, a natural sesquiterpenoid, induces apoptosis and growth arrest in HCT116 human colon cancer cells." J Pharmacol Sci 111(3): 276-284.

Katuru, R., N. V. Fernandes, et al. (2011). "Mevalonate depletion mediates the suppressive impact of geranylgeraniol on murine B16 melanoma cells." Exp Biol Med (Maywood) 236(5): 604-613.

McAnally, J. A., J. Gupta, et al. (2007). "Tocotrienols potentiate lovastatin-mediated growth suppression in vitro and in vivo." Exp Biol Med (Maywood) 232(4): 523-531.

Mo, H., M. Elfakhani, et al. (2013). Mevalonate-suppressive tocotrienols for cancer chemoprevention and adjuvant therapy. Tocotrienols: vitamin E beyond tocopherols. R. R. Watson, V. R. Preedy and B. Tan. Boca Raton, CRC Press: 135-149.

Mo, H. and C. E. Elson (1999). "Apoptosis and cell-cycle arrest in human and murine tumor cells are initiated by isoprenoids." J Nutr 129(4): 804-813.

Mo, H. and C. E. Elson (2004). "Studies of the isoprenoid-mediated inhibition of mevalonate synthesis applied to cancer chemotherapy and chemoprevention." Exp Biol Med (Maywood) 229(7): 567-585.

Mo, H. and C. E. Elson (2008). Role of the mevalonate pathway in tocotrienol-mediated tumor suppression. Tocotrienols: vitamin E beyond tocopherols. R. R. Watson and V. R. Preedy. Boca Raton, CRC Press: 185-207.

Oon, S. F., M. Nallappan, et al. (2015). "Xanthorrhizol: a review of its pharmacological activities and anticancer properties." Cancer cell international 15(1): 100.

Sever, N., B. L. Song, et al. (2003). "Insig-dependent ubiquitination and degradation of mammalian 3-hydroxy-3-methylglutaryl-CoA reductase stimulated by sterols and geranylgeraniol." J Biol Chem 278(52): 52479-52490.

Song, B. L. and R. A. DeBose-Boyd (2006). "Insig-dependent ubiquitination and degradation of 3-hydroxy-3-methylglutaryl coenzyme a reductase stimulated by δ- and γ-tocotrienols." J Biol Chem 281(35): 25054-25061.

Tallarida, R. J. (2006). "An overview of drug combination analysis with isobolograms." J Pharmacol Exp Ther 319(1): 1-7.

Yeganehjoo, H., R. DeBose-Boyd, et al. (2017). "Synergistic impact of d-δ-tocotrienol and geranylgeraniol on the growth and HMG CoA reductase of human DU145 prostate carcinoma cells." Nutr Cancer 69(4): 682-691.

The invention claimed is:

1. A method of treating inflammation in a patient in need thereof, comprising orally administering to the patient a composition of xanthorrhizol and tocochromanol in synergistically effective amounts, wherein the composition has a ratio of xanthorrhizol:tocochromanol from 1:10 to 10:1, wherein the composition does not comprise curcumin.

2. The method of claim 1, wherein the composition further comprises geranylgeraniol.

3. The method of claim 1, wherein the tocochromanol is a tocotrienol.

4. The method of claim 3, wherein the tocotrienol is an isomer of tocotrienol.

5. The method of claim 4, wherein the isomer of tocotrienol is δ-tocotrienol.

6. The method of claim 4, wherein the isomer of tocotrienol is γ-tocotrienol.

7. The method of claim 1, wherein the tocochromanol is a tocopherol.

8. The method of claim 1, wherein the tocochromanol is a synthetic tocochromanol.

9. The method of claim 1, wherein the tocochromanol is a natural tocochromanol.

10. The method of claim 3, wherein the tocotrienol is a natural tocotrienol.

11. The method of claim 7, wherein the tocopherol is a natural tocopherol.

12. The method of claim 1, wherein the xanthorrhizol is a synthetic xanthorrhizol.

13. The method of claim 1, wherein the xanthorrhizol is a natural xanthorrhizol.

14. The method of claim 1, wherein the composition has an effect with an Combination Index (CI) value lower than 1.

15. The method of claim 2, wherein the composition has an effect with an Combination Index (CI) value lower than 1.

16. The method of claim 1, wherein the tocochromanol is a mixture of one or more tocotrienol isomers.

17. A method of treating melanoma in a patient in need thereof, comprising orally administering to the patient a composition of xanthorrhizol and tocochromanol in synergistically effective amounts, wherein the composition has a ratio of xanthorrhizol:tocochromanol from 1:10 to 10:1, wherein the composition does not comprise curcumin.

* * * * *